(12) United States Patent
Dell'Oca

(10) Patent No.: US 8,353,910 B2
(45) Date of Patent: Jan. 15, 2013

(54) HIP HELICAL IMPLANT

(75) Inventor: Alberto A. Fernandez Dell'Oca, Montevideo (UY)

(73) Assignee: Synthes USA, LLC, West Chester, PA (US)

( * ) Notice: Subject to any disclaimer, the term of this patent is extended or adjusted under 35 U.S.C. 154(b) by 899 days.

(21) Appl. No.: 12/294,567

(22) PCT Filed: Apr. 20, 2007

(86) PCT No.: PCT/US2007/009739
§ 371 (c)(1),
(2), (4) Date: Nov. 13, 2008

(87) PCT Pub. No.: WO2007/124099
PCT Pub. Date: Nov. 1, 2007

(65) Prior Publication Data
US 2010/0063503 A1    Mar. 11, 2010

Related U.S. Application Data

(60) Provisional application No. 60/793,622, filed on Apr. 21, 2006.

(51) Int. Cl.
*A61B 17/72* (2006.01)
(52) U.S. Cl. ............................................. 606/64; 606/99
(58) Field of Classification Search .............. 606/62–68, 606/86–87, 96–99
See application file for complete search history.

(56) References Cited

U.S. PATENT DOCUMENTS

| 5,300,074 | A | * | 4/1994 | Frigg ................................ 606/67 |
| 5,454,813 | A | * | 10/1995 | Lawes .............................. 606/62 |
| 5,741,256 | A | | 4/1998 | Bresina |
| 5,810,821 | A | | 9/1998 | Vandewalle |
| 6,379,360 | B1 | * | 4/2002 | Ackeret et al. ................... 606/67 |
| 6,443,954 | B1 | * | 9/2002 | Bramlet et al. .................. 606/62 |
| 7,488,328 | B2 | * | 2/2009 | Gotfried .......................... 606/99 |
| 7,666,207 | B2 | * | 2/2010 | Schlapfer et al. ............. 606/246 |
| 2002/0133156 | A1 | | 9/2002 | Cole |
| 2005/0055024 | A1 | * | 3/2005 | James et al. ..................... 606/64 |

FOREIGN PATENT DOCUMENTS

| JP | 5-176942 | 7/1993 |
| JP | 2001507965 | 6/2001 |
| WO | 2004/039270 | 5/2004 |
| WO | 2005/025436 | 3/2005 |

* cited by examiner

*Primary Examiner* — Eduardo C Robert
*Assistant Examiner* — Steven Cotroneo
(74) *Attorney, Agent, or Firm* — Fay Kaplun & Marcin, LLP

(57) ABSTRACT

An intramedullary osteosynthetic device includes an intramedullary nail, a hip helical implant, a sliding sleeve, a lateral set screw, and a distal locking screw. The intramedullary nail includes an oblique slotted bore that receives the sliding sleeve and in communication with a cannulation that is partially threaded to receive a coaxial set screw and a threaded notch compatible with the lateral set screw. The hip helical implant includes a frontal helical portion, at least two helical twisted blades attached to the frontal helical portion, and a rear smooth shaft having an external flat surface. The sliding sleeve includes a tube having an internal flat corresponding to the external flat and has external threads at the rear of the sleeve engaging the lateral set screw. The coaxial set screw fixes the sliding sleeve to the intramedullary nail by tightening the sliding sleeve inside the oblique bore.

14 Claims, 15 Drawing Sheets

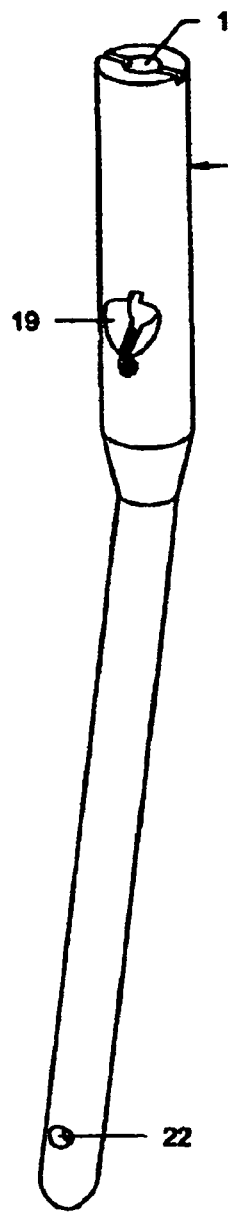
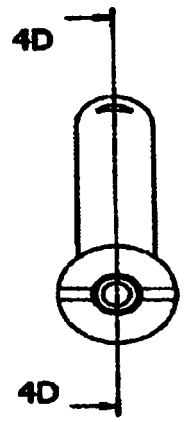
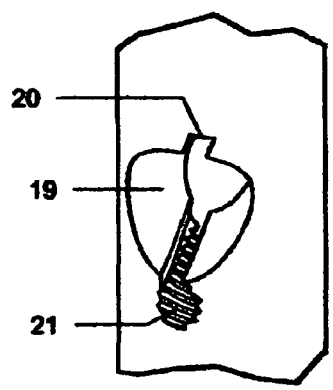
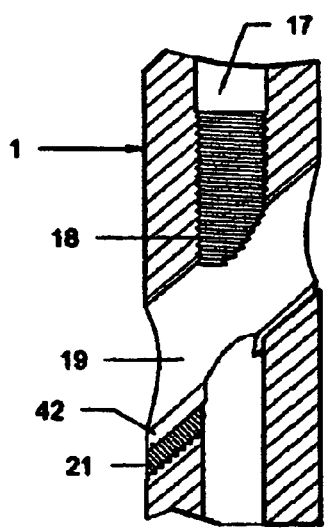
FIG. 4B
FIG. 4D
FIG. 4C
FIG. 4A

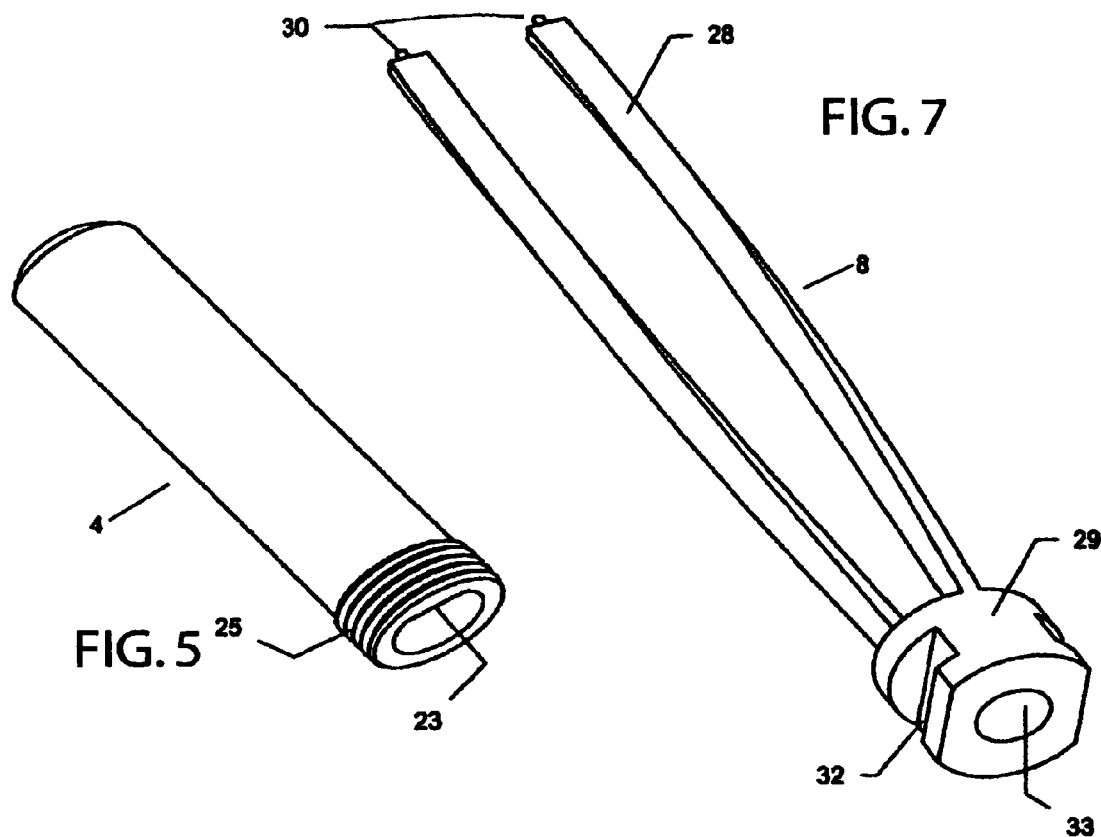
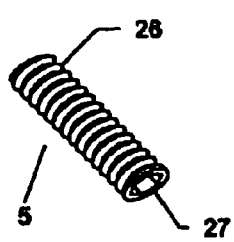
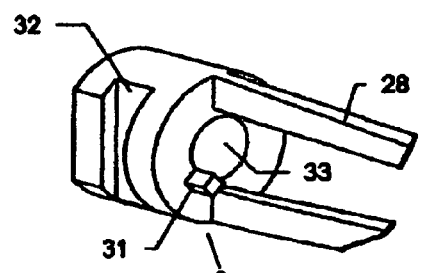

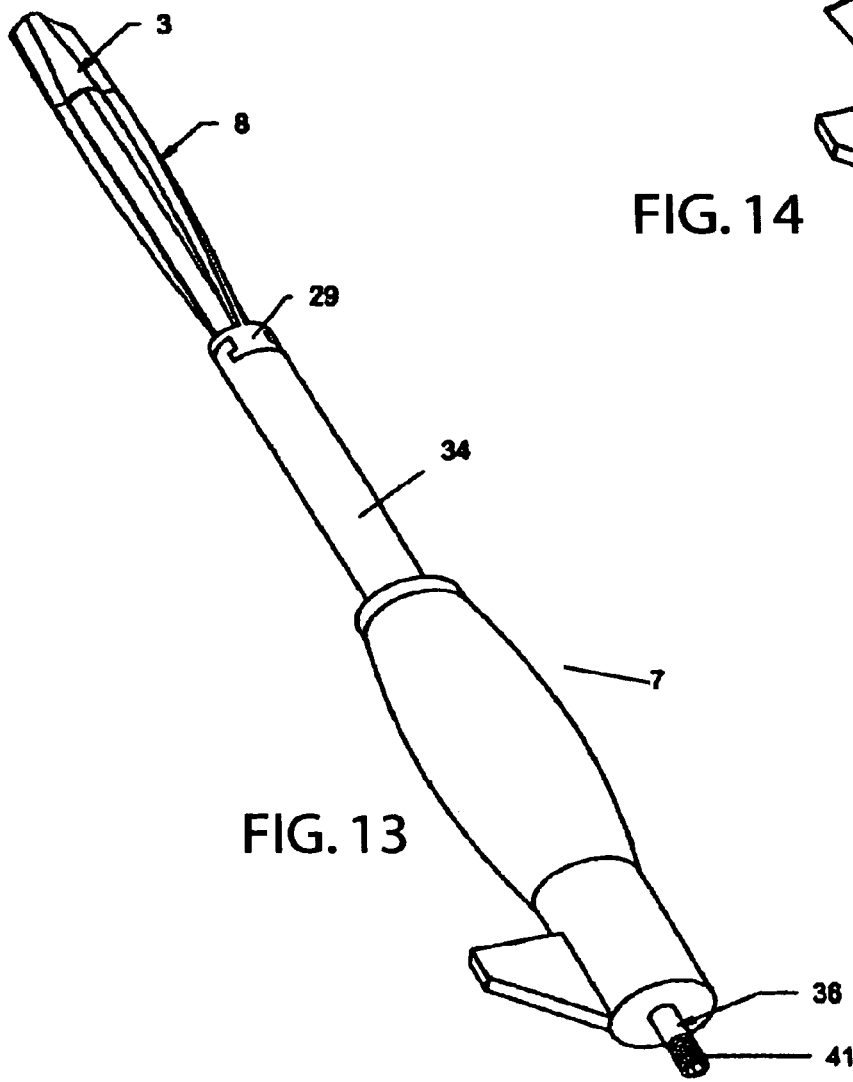
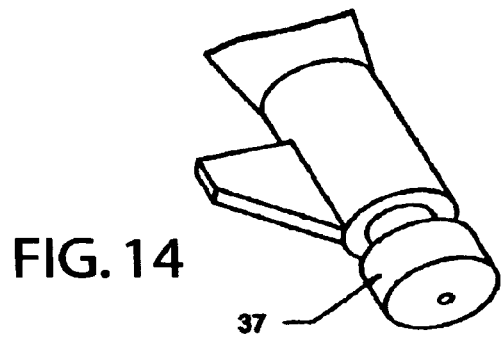
FIG. 13
FIG. 14

HIP HELICAL IMPLANT

FIELD OF THE INVENTION

The present invention relates to a device for use in osteosynthesis to treat femoral fractures, in particular fractures of the neck and the intertrochanteric region of the femur.

BACKGROUND OF THE INVENTION

Many implants have been developed to treat intertrochanteric femoral fractures which are basically based on a hip nail or screw that is inserted from the side of the femur through the neck and into the femoral head, and afterwards it is fixed either to an intramedullary nail positioned inside the femoral shaft, or to a side plate positioned in the outside of the femoral shaft.

In 1969 Zickel developed an intramedullary rod and cross nail assembly. U.S. Pat. No. 3,33,220 discloses a hip nail fixed to an intramedullary nail inside the femoral shaft. This device, while permitting an adequate fixation and rotational control of the fracture, was unable to allow sliding of the fracture's bone fragments towards each other along the hip nail. As a result, bone contact was insufficient to support a patient's weight, resulting in an increased risk of bending or breaking of the implanted hip nail. This, together with the shape of the hip nail, determinate too much pressure over the femoral neck and head bone tissue, could lead the implant to cut through the cancellouse tissue of the femoral neck or head in a condition known as "cut out", causing the nail to pierce the surface of the femoral neck or head, or at the least to lose proper alignment of the bone fracture.

To solve one of these difficulties, collapsible implants where developed. In these kinds of implants, the hip nail or screw is allowed to slide back through a bore in the side plate or intramedullary nail, permitting the migration of the bone fragments into each other, and therefore allowing the reduction of the fracture as the patient ambulates (bearing weight in the fractured limb). This allows for increased bone contact, tolerating more pressure and therefore minimizing the tendency of breaking the hips' implant. An example of these implants is Lawes intertrochanteric fracture fixation device, disclosed in U.S. Pat. No. 5,176,681. However, these implants have a small horizontal surface to contact with bone tissue. Thus, when the healing bone is under the patients' weight, the implant may cut through the cancellous bone of the femoral head, causing the implant to rupture the femoral surface, or to no longer maintain a proper alignment of the fracture. Another disadvantage of these types of implants is that they lack rotational control, permitting the rotation of the femoral head around the hip screw.

Thereafter, complete helical blades were developed, such as Neufelds' Subtrochanteric Nail described in U.S. Pat. No. 4,103,683; and Friggs' Fixation Plate disclosed in U.S. Pat. No. 4,978,349, which consist in a single helical blade that is inserted through the femoral neck into the femoral head, so that when the insertion is completed the distal end of the blade lies in a vertical position passing through a vertical slot in the intramedullary nail; while the proximal end lies in a horizontal position, permitting the load to be dispersed over the femoral head and act on a larger and flat surface. This diminishes the pressure on the bone tissue, thus reducing the tendency of the implant to cut out after implantation. Although this may solve the cutting out problem and achieve adequate rotational stability, this system does not allow the sliding back of the implant through the vertical slot in the intramedullary nail, and therefore fails to permit the necessary bone fragment migration needed to provide fracture compression.

In order to obtain the necessary sliding (minimizing the implants' breaking risk, while permitting compression of bone fragments), and to avoid the cutting-out problem of complete helical implants, partial helical implants were developed. Examples of these implants are the Two-part Angle Plate invented by Frigg U.S. Pat. No. 5,300,074, and Bresinas' Helical Implant U.S. Pat. No. 5,908,422. In these devices the hip implant consists of a proximal helical blade at the front portion of the implant (which increases the surface over which the load acts, preventing the cut-out), followed by a distal shaft at the rear portion of the implant which is able to slide back through the bore in the intramedullary nail or side plate. The shaft needed to permit sliding does not allow rotational control, which may result in the rotation of one bone fragment around another. In addition, partial helical implants have an additional draw-back: the helical implant needs to be inserted in a guided way that permits the implant to rotate in a constant and predetermined rhythm, otherwise the implant would provoke femoral neck and head tissue loss while being inserted, and as a consequence the fracture fixation may become unstable, mainly in osteoporotic bones. Therefore, an outside guide (outrigger) is required to guide the insertion of this partial helical implants. Such a design and use is very complex.

Accordingly, a need exists to develop an osteosynthetic implant to treat intertrochanteric femoral fractures that minimizes the tendency to cut through the femoral head and neck tissue after insertion, that permits sliding, maintaining rotational control; and that has an easy guided insertion, without the need of an outrigger.

SUMMARY OF THE INVENTION

It is an object of the present invention to provide an intramedullary osteosynthetic device to treat proximal femoral fractures, which has minimal tendency to cut out through the cancellous femoral bone tissue once inserted; allows sliding back of the hip implant to permit the approaching of bone fragments; and is rotationally stable.

It is another object of the invention to develop an insertion tool to guide the implants insertion, which has simple design and easy technique.

It is a further objective of the present invention to provide a hip implant that permits its easy removal by a single lateral approach, should it be required.

To fulfill these objectives the present invention consists of multiple individual components: an intramedullary nail with optional distal locking screws, a hip helical implant, a sliding sleeve, a lateral set screw, and an optional coaxial set screw; as well as an insertion tool and a step helix. These last two components may be used during an insertion procedure.

The hip helical implant is a partial helical implant that consists of a frontal (distal) helical portion, and a rear (proximal) smooth shaft. The frontal helical portion is provided with at least two helically twisted blades, designed to prevent the cutting-out problem after insertion in the femoral head. The rear smooth shaft fits into the sliding sleeve, permitting the sliding-back of the implant through the sleeve. In order to achieve rotational stability of the implant, the shaft of the hip helical implant has a flat that abuts an internal flat in the sliding sleeve, which prevents rotation of the shaft of the hip helical implant inside the sliding sleeve.

The intramedullary nail may be cannulated and has at least one oblique slotted bore proximate to its trailing end. This oblique bore is angled in the direction of the femoral neck, and is designed to accommodate the sliding sleeve, that slidably passes through it. In addition, the oblique bore may have at least two slots designed to accommodate the edges of the blades of the hip helical implant during the insertion procedure, in order to guide its insertion. Below the oblique bore, and in communication with it, the intramedullary nail is provided of a threaded notch to accommodate the lateral set screw, which provides fixation of the sliding sleeve to the intramedullary nail by a threaded mechanism.

To obtain a simple insertion technique that permits inserting the partial helical implant without the loss of bone tissue, a step helix is developed. The step helix consists of at least two helically twisted blades (same number as the blades in the hip helical implant) attached to a base at its rear (proximal) end. During the insertion procedure, the step helix is solidly fixed to the hip helical implant, in such a way that when assembled one with the other, the combination constitutes a temporarily complete helical assembly. This permits that during insertion, the hip helical implant turns in a constant pace and rhythm, and the guidance by the slots at the intramedullary nail as it advances towards the femoral head until its final position diminishes the bone loss provoked during insertion. When insertion is completed, the step helix is removed, leaving only the hip helical implant inside the femoral neck, which, having a rear smooth shaft, is able to slide back inside the sliding sleeve, thus permitting fracture compression.

An insertion tool allows for an easier insertion procedure. The insertion tool consists of a cannulated shaft with a rotating handle that is able to turn around the shaft; an axial insert that goes inside the cannulation in the shaft; and a rear cap that engages the rear end of the axial insert. Before insertion, the step helix is solidly engaged with the hip helical implant, from behind, constituting the helical assembly. Thereafter, the insertion tool is attached to the rear end of the helical assembly. This permits a proper engagement of the insertion tool with the step helix and the hip helical implant enabling an appropriate insertion procedure.

During the insertion procedure, the rear end of the insertion tool is hammered, pushing the helical assembly forward through the oblique bore of the intramedullary nail (previously introduced in the medullary canal) towards the femoral head. The slots at the oblique bore guide the insertion of the helical assembly; this, together with the affixing of the step helix to the hip helical implant, allows the helical implant to turn in a constant pace and rhythm as it advances during the insertion procedure, causing the minimal bone loss.

After insertion is completed, the step helix and the insertion tool are easily removed., leaving the hip helical implant, and the sliding sleeve is introduced over the shaft of the hip helical implant and through the oblique bore of the intramedullary nail, permitting sliding back of the hip helical implant through the sleeve. This provides rotational stability due to the above described flats. Thereafter, a lateral set screw is inserted in the notch of the intramedullary nail affixing the sliding sleeve to the nail.

BRIEF DESCRIPTION OF THE DRAWINGS

The intramedullary osteosynthetic device is explained in even greater detail in the following exemplary drawings. The intramedullary osteosynthetic device may be better understood by reference to the following drawings, wherein like references numerals represent like elements. The drawings are merely exemplary to illustrate the structure, operation and method of use of the intramedullary osteosynthetic device and certain features that may be used singularly or in combination with other features and the invention should not be limited to the embodiments shown.

The invention is explained in more detail schematically and by way of example with reference to figures:

FIG. 4A, is a perspective view of an intramedullary nail.

FIG. 4B, is a top view of the intramedullary nail depicted in FIG. 4A.

FIG. 4C, is an enlarged perspective view of the oblique opening of the intramedullary nail depicted in FIG. 4A.

FIG. 4D, is a cross sectional view of the intramedullary nail depicted in FIG. 4A taken on line 4D-4D of FIG. 4B.

FIG. 5, is a perspective view of a sliding sleeve.

FIG. 6, is a perspective view of a lateral set screw.

FIG. 7, is a perspective view of a step helix.

FIG. 7A, is an enlarged perspective view of the base of the step helix depicted in FIG. 7.

FIG. 13 is a perspective view of the hip helical implant, assembled with the step helix and the insertion tool after introducing the axial insert.

FIG. 14, is a perspective view of the rear portion of the insertion tool with a cap in it.

DETAILED DESCRIPTION OF THE PREFERRED EMBODIMENTS

Figure 1:
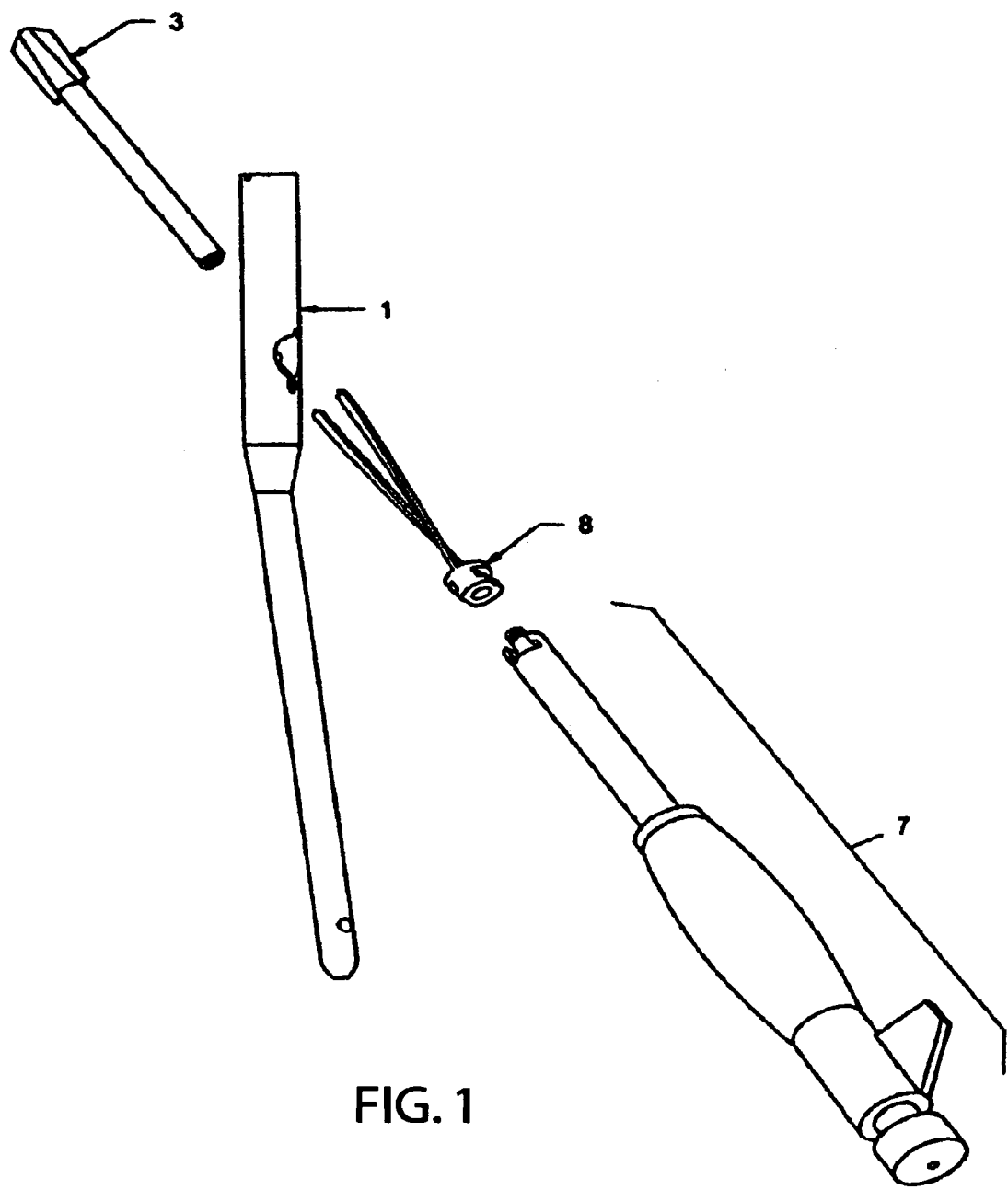
FIG. 1, is a perspective view of some of the components of the preferred embodiment of the present invention, in an exploded state.
Figure 2:
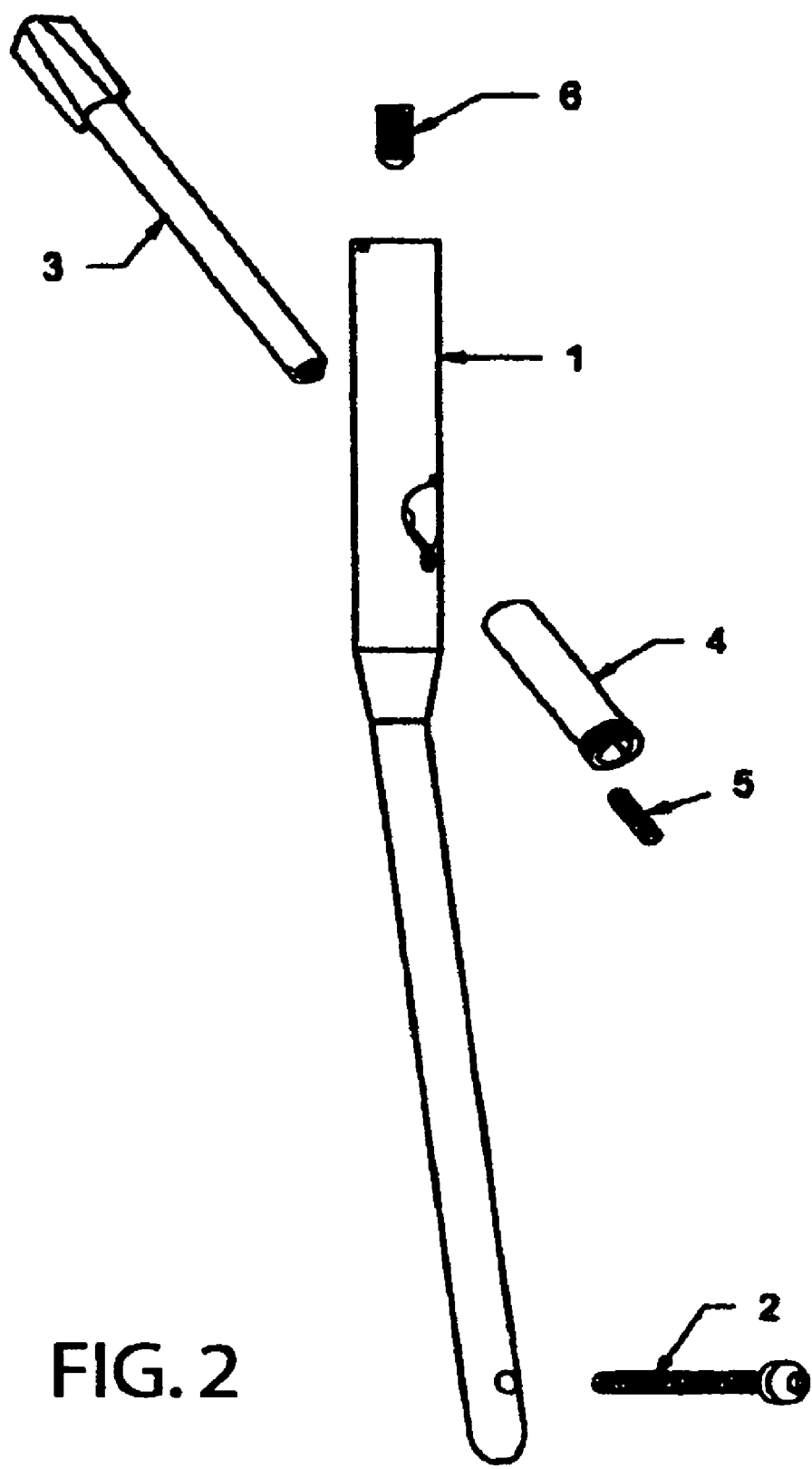
FIG. 2, is a perspective view of the components of the preferred embodiment depicted in FIG. 1, in an exploded state.

FIGS. 1 and 2 illustrate individual components of a preferred embodiment of the intramedullary ostesynthetic device, which includes an intramedullary nail 1 with optional distal locking screws 2, a hip helical implant 3, a sliding sleeve 4, a lateral set screw 5, and an optional coaxial set screw 6; as well as an insertion tool 7 and a step helix 8. The insertion tool 7 and step helix 8 may be used during the insertion procedure.

Figure 3:
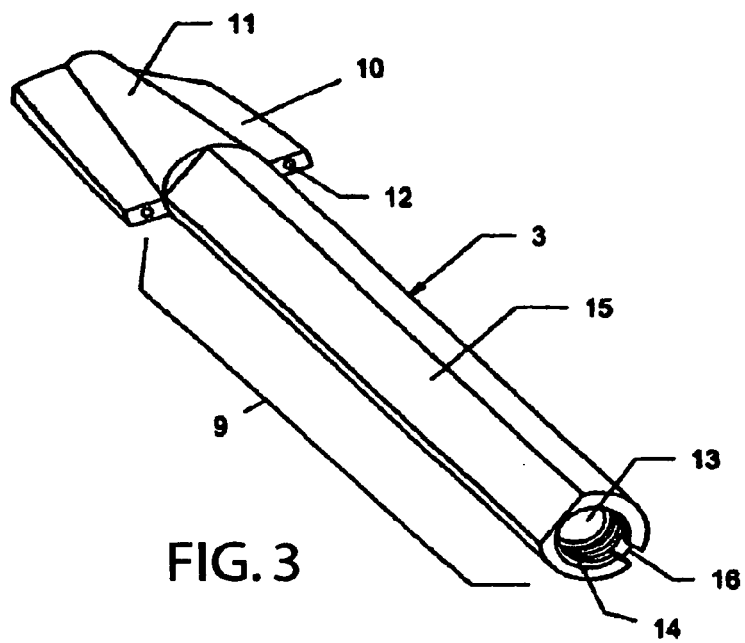
FIG. 3, is a perspective view of a hip helical implant.
Figure 3A:
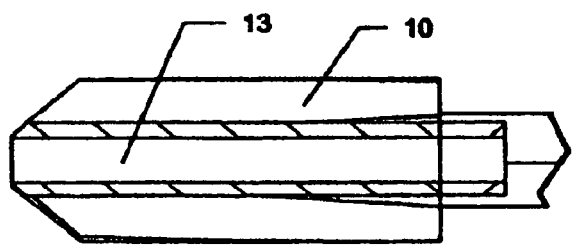
FIG. 3A, is a top view partially in cross section of the front portion of the hip helical implant depicted in FIG. 3.
Figure 3B:
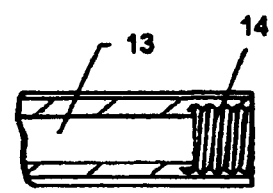
FIG. 3B, is a side view partially in cross section of the rear end of the hip helical implant depicted in FIG. 3.

FIGS. 3 to 3B illustrate a preferred embodiment of the hip helical implant 3, which consists of a front helical portion 11, and a rear smooth shaft 9. The frontal helical portion 11 is provided of at least two helically twisted blades 10, which are attached to the axis of the front helical portion 11 that has a truncated conical shape. Additional blades are contemplated. Each blade 10 is provided with a hole 12 at its rear end, designed to receive the pegs 30 located at the frontal ends of the step blades 28 of the step helix 8 (FIG. 7), in order to allow a solid fixation between the blades 10 of the helical implant 3 and the step blades 28. The helical implants' shaft 9 may be cannulated to receive a Kirschner wire during insertion procedure; the cannulation 13 may have an internally threaded rear portion 14 designed to receive the axial insert 36 of the insertion tool 7. The shaft 9 of the hip helical implant 3 may have an external flat 15 that abuts an internal flat 23 located in the sliding sleeve 4 to prevent rotation while permitting sliding of the hip helical implant 3 inside the sliding sleeve 4. Furthermore, at its rear end, the shaft 9 may be provided with a notch 16 to accommodate a frontal peg 31 located in the base of the step helix 8 in order to improve fixation of the step helix 8 to the hip helical implant 3.

The intramedullary nail 1 (FIGS. 4A to 4D), may be cannulated 17. The cannulation 17 may be provided with a threaded portion 18 in order to receive an optional coaxial set screw 6. At least one oblique slotted bore 19, in communication with the cannulation 17, is designed to receive the sliding sleeve 4. The oblique bore 19 may have at least two slots 20 and 42 designed to accommodate the edges of the blades 10 of the hip helical implant 3 in order to guide its insertion. Below (more distal than) the oblique bore 19 and in communication with it, the intramedullary nail 1 is provided with a threaded notch 21 designed to accommodate a lateral set screw 5 (FIGS. 4C and 4D). The oblique bore 19 with its slots 20 and 42, and the threaded notch 21, are angled so that when the intramedullary nail 1 is positioned inside the medullary canal of the femur, the axis of the slots and notch is directed towards the axis of the femoral neck (FIG. 4D). Additionally, the intramedullary nail 1 may have distal transverse bores 22 to receive optional distal locking screws 2.

The sliding sleeve 4, which is shown in FIG. 5, consists in a tube that has an internal flat 23 designed to abut the external flat 15 on the shaft 9 of the hip helical implant 3. At its rear end the sleeve 4 may be externally treaded 25 in order to engage the lateral set screw 5, which affixes the sliding sleeve 4 to the intramedullary nail 1. The sliding sleeve 4 slidably passes through the oblique bore 19 of the intramedullary nail 1 and is fixed to it by a lateral set screw 5.

The lateral set screw 5 is illustrated in FIG. 6 and may have an external thread 26 that engages the rear threaded portion 25 of the sliding sleeve 4, affixing the sliding sleeve 4 to the intramedullary nail 1. The lateral set screw 5 is also provided of an hexagonal hole 27 at its rear edge to accommodate an hexagonal screwdriver. Other configurations of the hole 27 are contemplated. 100561 Alternatively, an optional coaxial set screw 6 (shown in FIG. 2) may be used to accomplish the fixation of the sliding sleeve 4 to the intramedullary nail 1. The coaxial set screw 6 may be inserted into the internally threaded cannulation 18 of the intramedullary nail 1 in order to tighten up the sliding sleeve 4 inside the oblique bore 19 of said intramedullary nail 1.

FIGS. 7 and 7A illustrate the preferred embodiment of the step helix 8 which consists of at least two (same number as the blades of the hip helical implant 3) helically twisted step blades 28 attached at its rear end to a slotted base 29. The step blades 28 engage with the rear end of the blades 10 of the hip helical implant 3 by means of pegs 30 located at the frontal edge of the step blades 28, which fit into the holes 12 at the rear edge of the blades 10 of the hip helical implant 3. The base 29 of the step helix 8 may be provided with a frontal peg 31 at its top, which fits into the rear notch 16 located at the rear end of the shaft 9 of the hip helical implant 3. Furthermore, the base 29 is provided with a lateral slot 32, shown in FIG. 7A, that accommodates the insertion tool 7. Moreover, the base 29 may be cannulated 33 to permit the axial insert 36 of the insertion tool 7 to pass through this cannulation 33 in order to engage the rear part of the hip helical implant 3.

Figure 8:
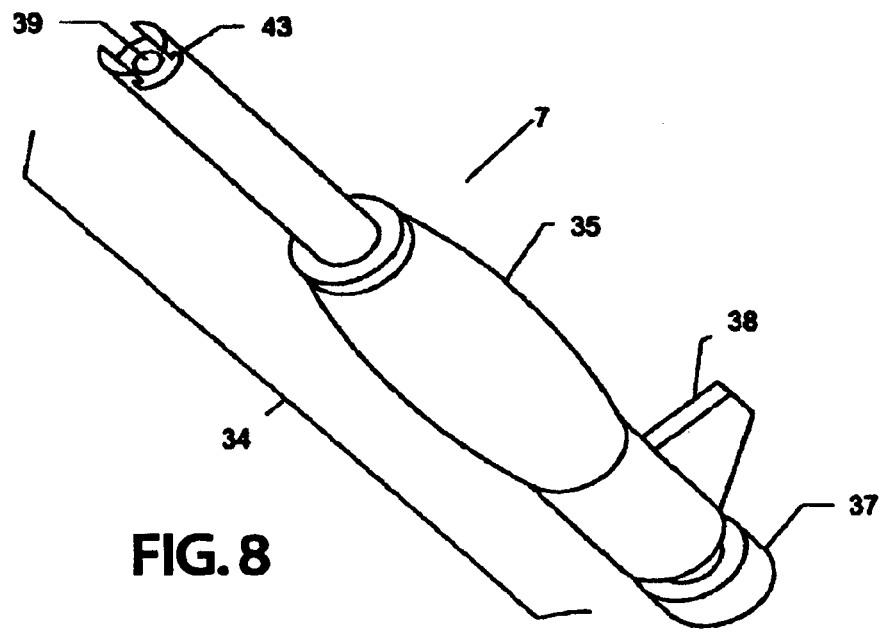
FIG. 8, is a perspective view of an insertion tool before introducing an axial insert through it.
Figure 9:
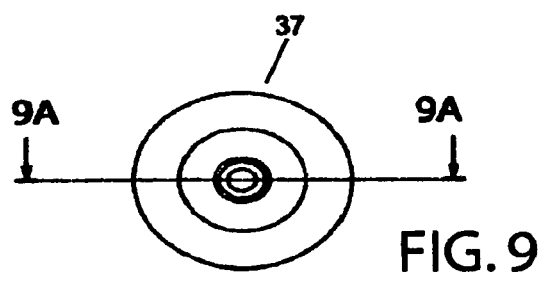
FIG. 9, is a top view of the cap of the insertion tool depicted in FIG. 8.
Figure 9A:
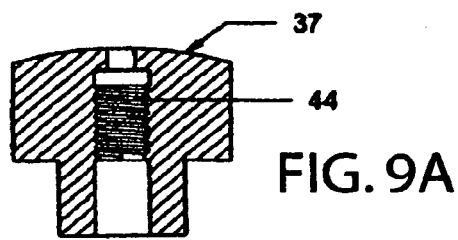
FIG. 9A, is a cross section of the cap of the insertion tool taken on line 9A-9A of FIG. 9.
Figure 9B:
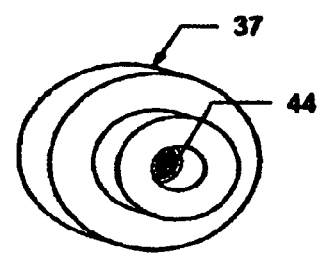
FIG. 9B, is a perspective view of the cap of the insertion tool depicted in FIG. 8.
Figure 10:
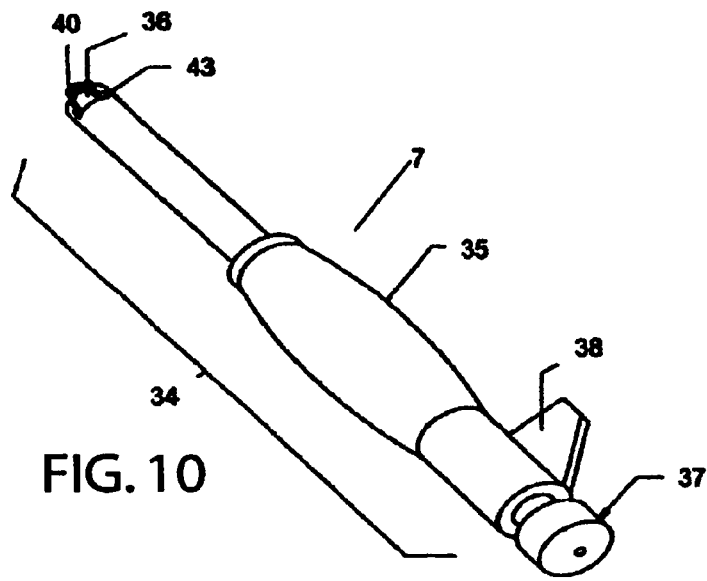
FIG. 10, is a perspective view of the insertion tool with all its components.
Figure 10A:
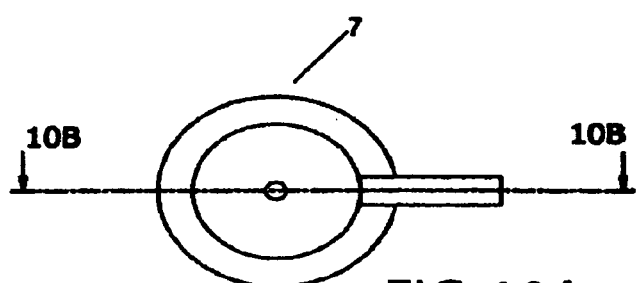
FIG. 10A, is a bottom end view of the insertion tool depicted in FIG. 10.
Figure 10B:
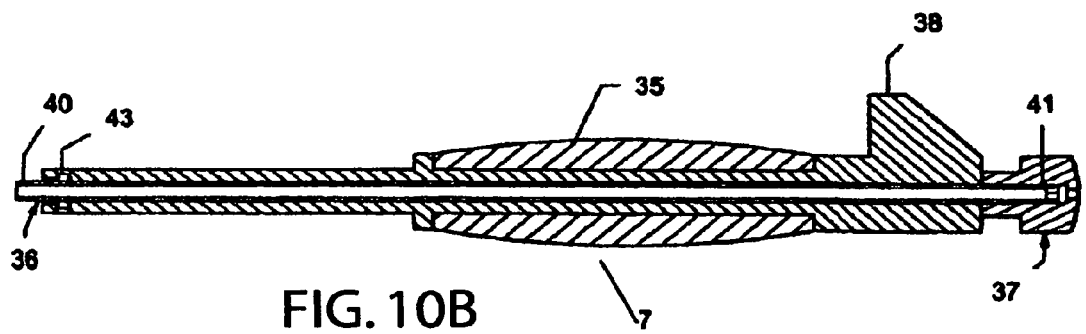
FIG. 10B, is a cross section of the insertion tool taken on line 10B-10B of FIG. 10A.

The insertion tool 7 is illustrated in FIGS. 8 to 10B. The insertion tool 7 consists of a cannulated shaft 34 with a rotating handle 35, an axial insert 36, and a rear cap 37. The rotating handle 35 is assembled over the shaft 34 in a manner that permits the handle 35 to rotate around the longitudinal axis of the shaft 34. The cannulated shaft 34 may have a slot 43 at its frontal end, designed to engage with the lateral slot 32 at the base 29 of the step helix 8. The rear portion of the shaft 34 is provided with a nose 38 which is hammered backwards in order to remove the insertion tool 7 after insertion is completed. Moreover, the shaft 34 may be cannulated 39 (as shown in FIGS. 8 and 10B) in order to receive the axial insert 36. The axial insert 36, shown in FIGS. 10 and 10B is a tube with a smaller diameter than the shaft of the insertion tool 34, so as to be able to slidably pass through the cannulation 39 of the shaft 34. The axial insert 36 may have an externally threaded frontal end 40 designed to engage the internal thread 14 at the shaft 9 of the hip helical implant 3 firmly attaching one another during the insertion procedure. Furthermore, the axial insert 36 may have an externally threaded rear end 41 designed to engage the internally threaded hole 44 of the rear cap 37 of the insertion tool 7 (illustrated in FIGS. 9 to 9B), in order to improve fixation of the insertion tool 7 to the helical implant 3.

Figure 11:
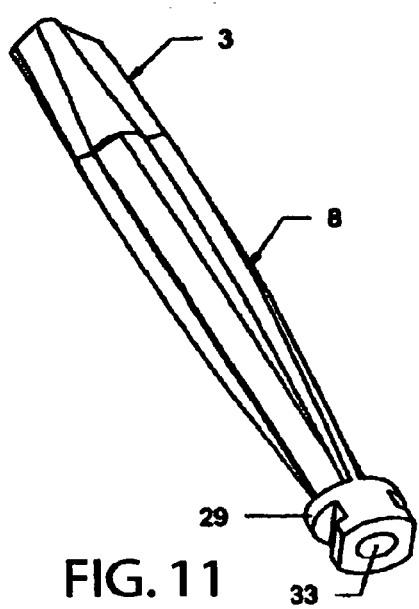
FIG. 11, is a perspective view of a hip helical implant assembled with a step helix.
Figure 12:
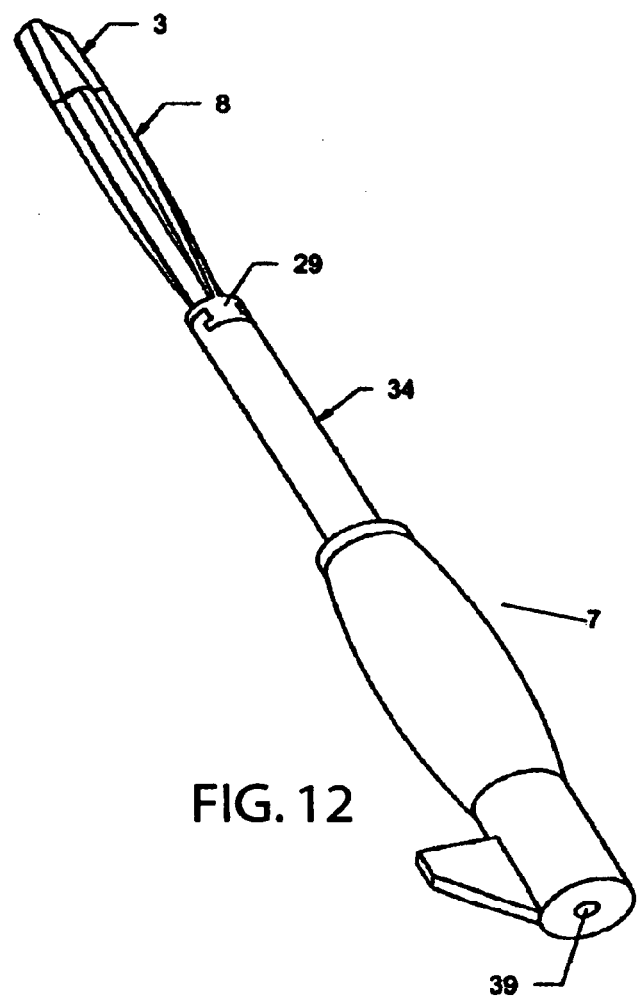
FIG. 12, is a perspective view of the hip helical implant, assembled with the step helix and an insertion tool without an axial insert and the cap.

The insertion tool 7 is assembled with the step helix 8 and the hip helical implant 3 before insertion. The assembly procedure is illustrated in FIGS. 11 to 14. In a first step, the step helix 8 is firmly assembled to the rear portion of the hip helical implant 3 constituting a temporary complete helix, as illustrated in FIG. 11. Thereafter, the shaft 34 of the insertion tool 7 is engaged to the base 29 of the step helix 8 by a slotted mechanism 32, 43, as shown in FIG. 12. The axial insert 36 of the insertion tool 7 is introduced through the cannulation 39 of the shaft 34 of the insertion tool 7, as illustrated in FIG. 13. The frontal threaded end 40 of the axial insert 36 passes through the cannulation 33 of the base 29 of the step helix 8, and into the internally threaded hole 14 in the shaft 9 of the hip helical implant 3. Thereafter, the axial insert 36 is threaded in the hip helical implant 3. The final step of the assembling procedure is illustrated in FIG. 14, where the cap 37 of the insertion tool 7 is attached to the rear threaded end 41 of the axial insert 36 by the internally threaded hole 44 of the cap 37. This allows a proper engagement of the insertion tool 7 with the step helix 8 and the hip helical implant 3 during the insertion procedure.

Figure 15:
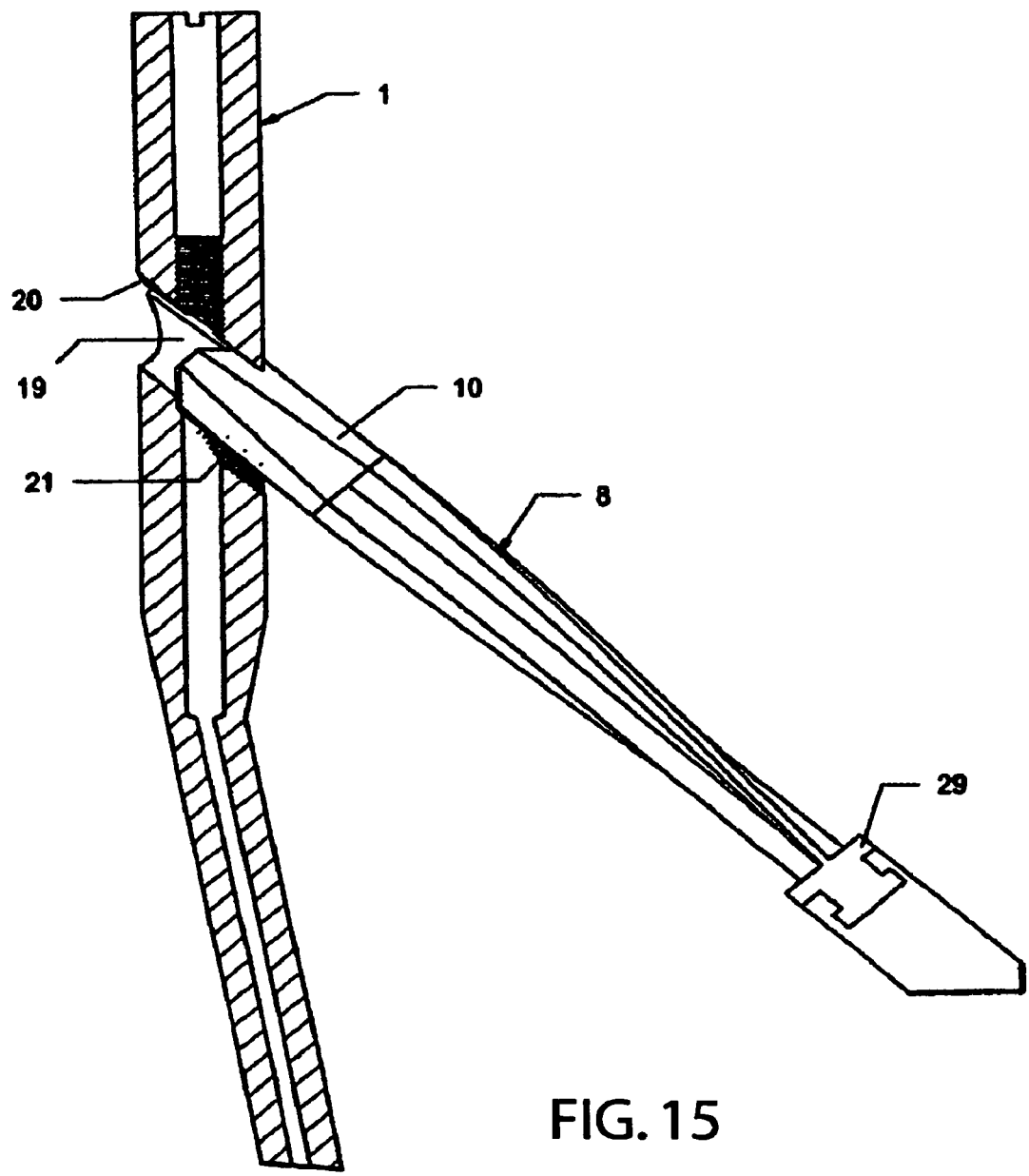
FIG. 15, is a side view of the insertion procedure, with the intramedullary nail in cross section, showing the hip helical implant passing through the intramedullary nail oblique opening.
Figure 16:
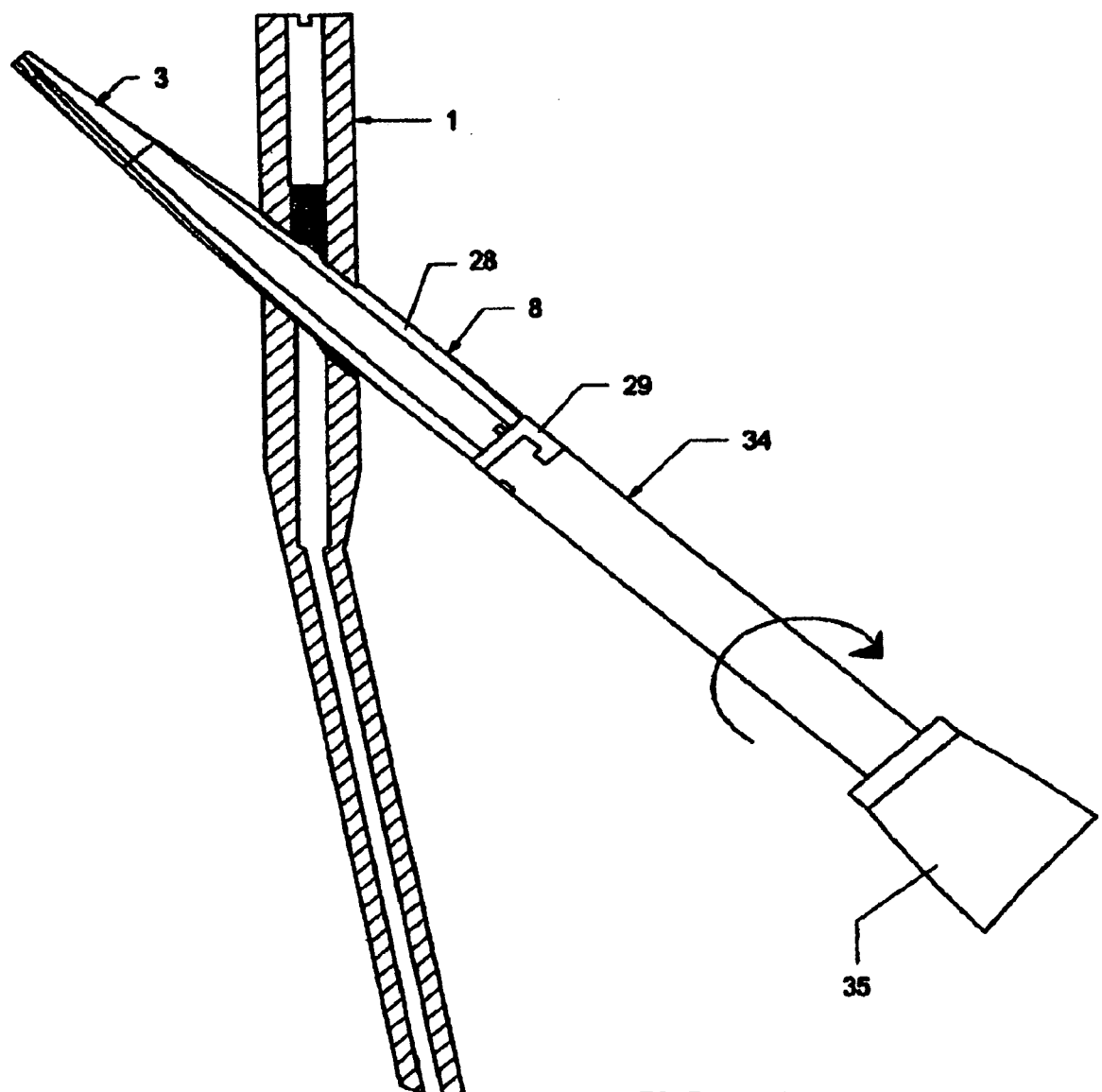
FIG. 16, is a side view during the insertion procedure, with the intramedullary nail in cross section, showing the step helix passing through the intramedullary nail oblique opening.

FIGS. 15 to 21 illustrate the insertion procedure of the intramedullary osteosynthetic device. In a first step, the intramedullary nail 1 is introduced inside the femoral medullary canal, in a manner consistent with common techniques. Then, the hip helical implant 3 is introduced through the oblique bore 19 of the intramedullary nail 1, so that the blades 10 of the hip helical implant 3 pass through the slots 20 and 42 of the intramedullary nail 1, which guide the insertion of the hip helical implant 3, as illustrated in FIG. 15. Thereafter, the step blades 28 of the step helix 8 pass through the same slots of the intramedullary nail and in the same direction than the hip helical implant 3, as shown in FIG. 16, until the hip helical implant 3 reaches its final position inside the femoral head. This permits that during insertion the hip helical implant 3 turns at a constant pace and rhythm as it advances towards the femoral head until it reaches its final position, guided by the slots 20, 42 in the intramedullary nail 1. During insertion, it may be necessary to hammer the rear (proximal) end of the insertion tool 7, advancing the helical assembly through the oblique bore 19 of the intramedullary nail 1 towards the femoral head. During this procedure, the rotating handle 35 of the insertion tool 7, enables the surgeon to hold the insertion tool 7 without the need to turn his wrist as the shaft 34 of the insertion tool 7 rotates, following the rotation that the hip helical implant 3 experiences during its insertion, as shown in FIG. 16.

Figure 17:
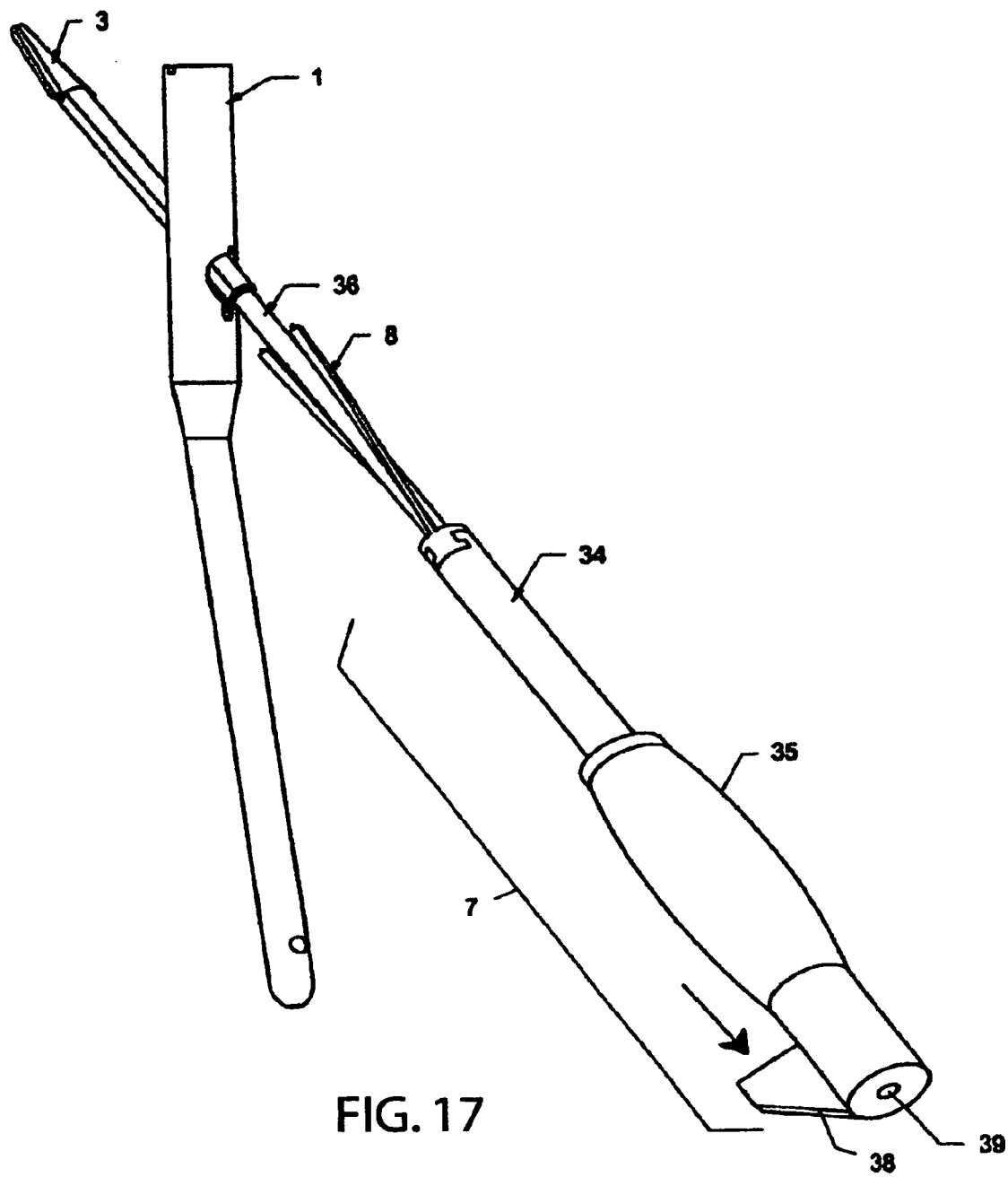
FIG. 17, is a perspective view of the removal of the insertion tool and step helix.
Figure 18:
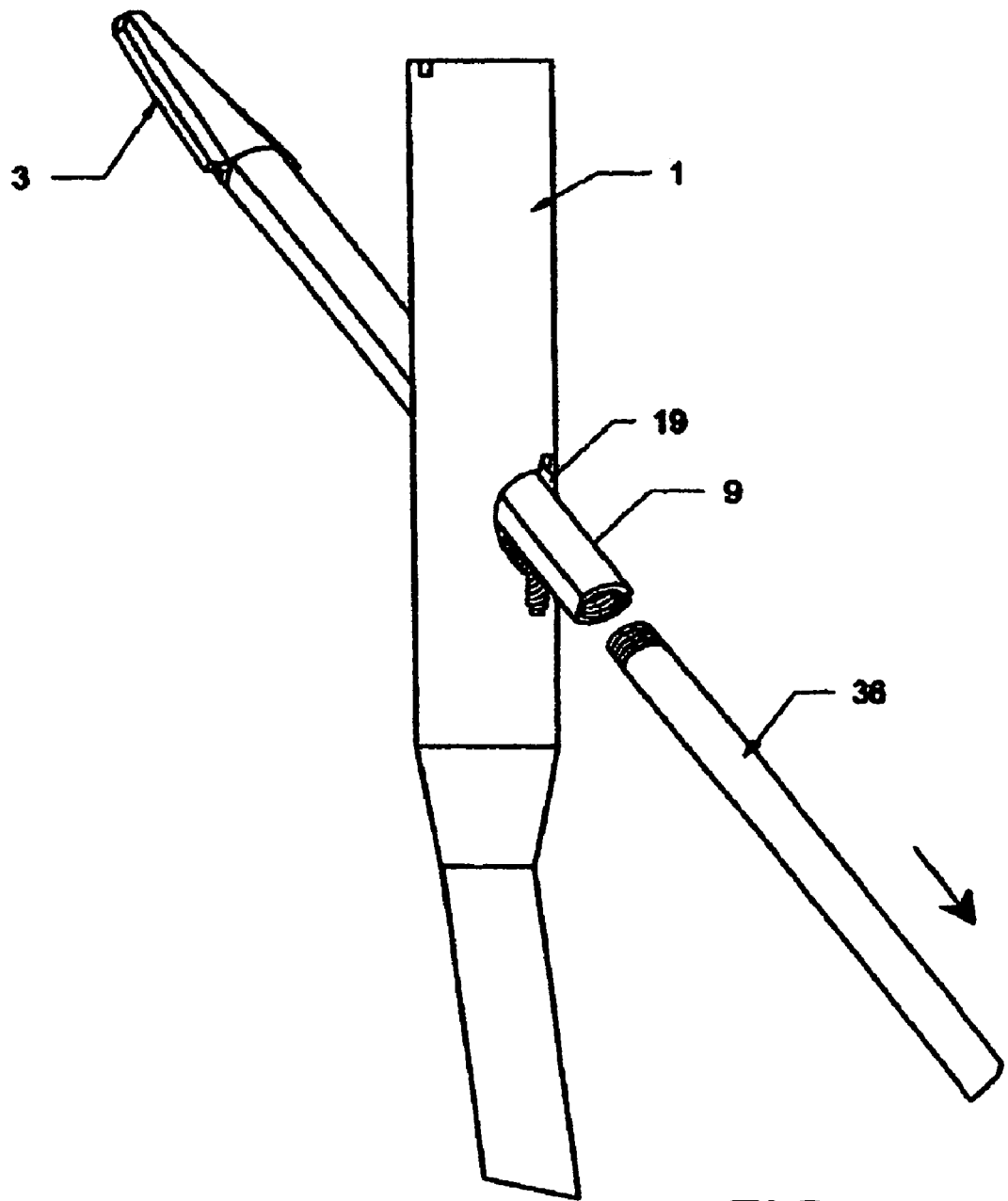
FIG. 18 is a perspective view showing the removal of the axial insert of the insertion tool from the hip helical implant, during the insertion procedure.

After insertion is completed, the step helix 8 and the insertion tool 7 are removed. This procedure is illustrated in FIGS. 17 and 18. In a first step the rear cap 37 of the insertion tool 7 is removed; thereafter, the nose 38 of the shaft of the insertion tool 7 is hammered backwards, causing the shaft 34 of the insertion tool 7 and the step helix 8 attached to it to slide back over the axial insert 36 of the insertion tool, as shown in FIG. 17, leaving only the axial insert 36 attached to the hip helical implant 3. In a last step, illustrated in FIG. 18, the axial insert 36 is unscrewed from the hip helical implant 3, leaving only the hip helical implant 3 inside the femoral neck with the shaft 9 of the hip helical implant 3 passing through the oblique bore 19 of the intramedullary nail 1.

Figure 19:
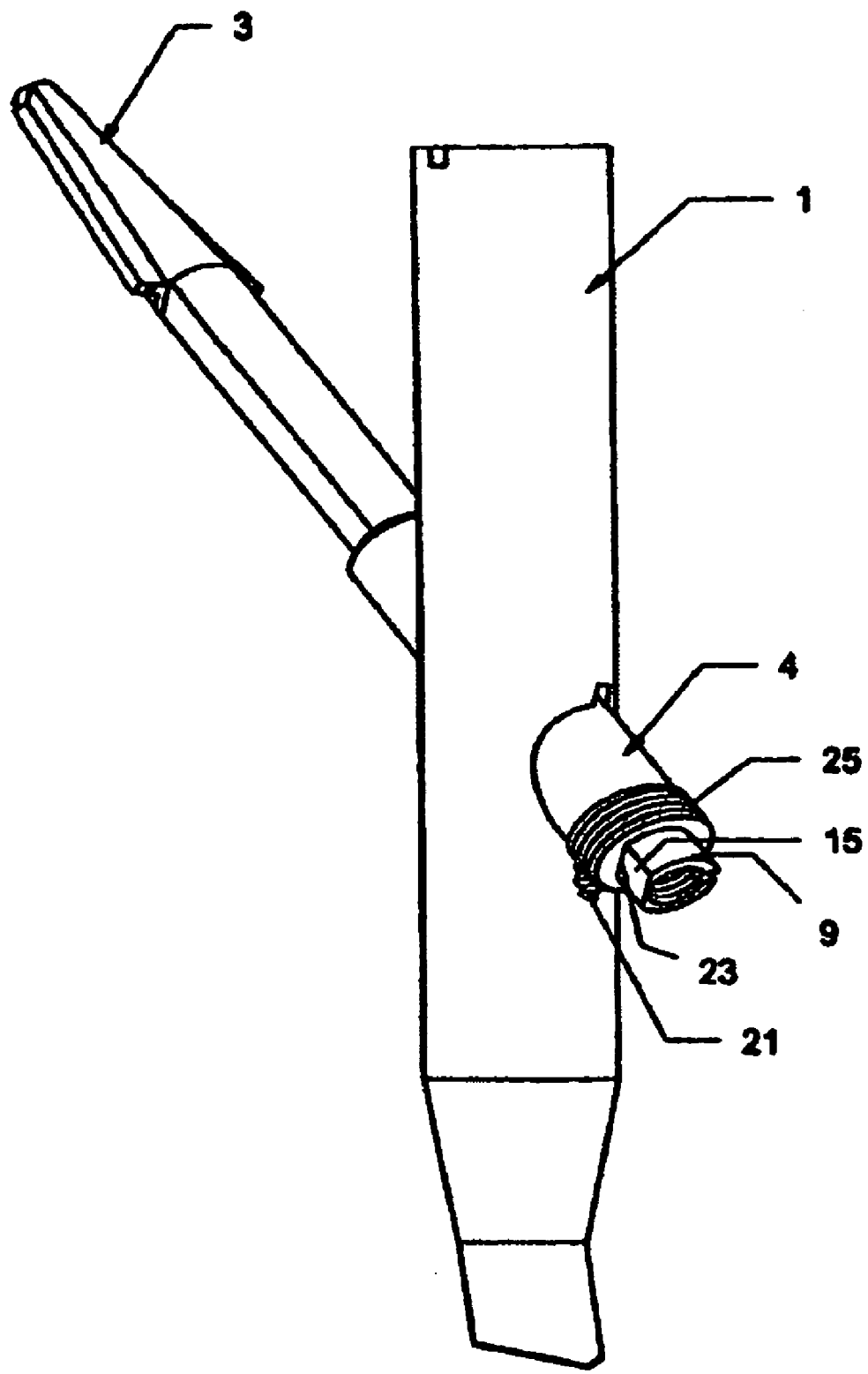
FIG. 19, is a perspective view during the insertion procedure, after the insertion of the sliding sleeve.
Figure 20:
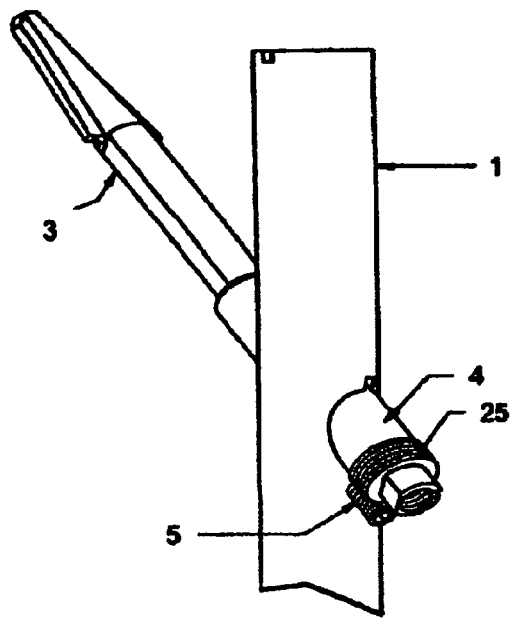
FIG. 20, is a perspective view of the final position after insertion of the lateral set screw.
Figure 21:
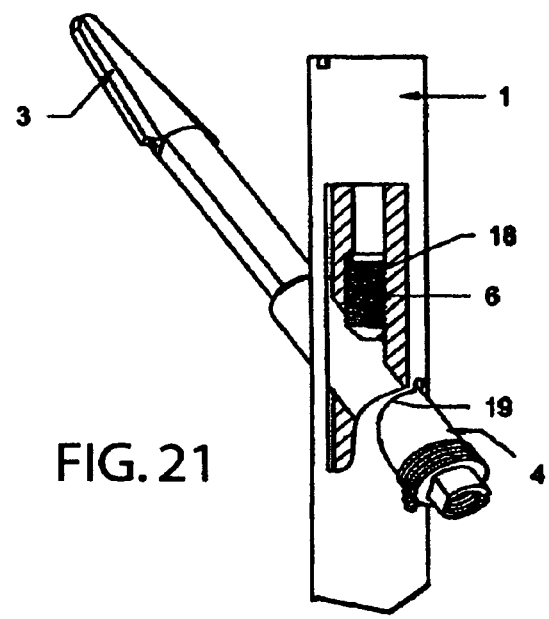
FIG. 21, is a perspective view, partially in cross section, of the final position with the insertion of the optional coaxial set screw.

Thereafter, the sliding sleeve 4 is pushed over the shaft 9 of the hip helical implant 3 so that the internal flat 23 of the sliding sleeve 4 abuts the flat 15 of the hip helical implant 3, passing through the oblique bore 19 of the intramedullary nail 1 towards the femoral neck, as illustrated in FIG. 19. This permits the sliding backwards of the hip helical implant 3 through the sliding sleeve 4, while allowing rotational stability. In order to affix the sliding sleeve 4 to the intramedullary nail 1, the lateral set screw 5 is introduced at the oblique threaded notch 21 in the intramedullary nail 1 engaging the externally threaded end 25 of the sliding sleeve 4 and affixing it to the intramedullary nail 1 as shown in FIG. 20. Another mechanism to affix the sliding sleeve 4 to the intramedullary nail 1 is to introduce a coaxial set screw 6 inside the treaded cannulation 18 of the intramedullary nail 1 downwards, towards the sliding sleeve 4, so that to tighten the sliding sleeve 4 up, inside the oblique bore 19, as illustrated in FIG. 21.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed:

1. An intramedullary osteosynthetic device comprising:
   an intramedullary nail;
   a hip helical implant;
   a sliding sleeve;
   a lateral set screw; and
   at least one distal locking screw;
   wherein the hip helical implant has an external flat corresponding to an internal flat in the sliding sleeve; and
   wherein the hip helical implant comprises:
      a frontal helical portion having a truncated conical shape;
      at least two helical twisted blades attached to the frontal helical portion; and
      a rear smooth shaft, the shaft having the external flat,
      wherein each blade has a hole for receiving a peg from a step for fixating the hip helical implant to the step helix, and
      the hip helical implant is cannulated to receive a Kirschner wire.

2. An intramedullary osteosynthetic device according to claim 1, wherein:
   the intramedullary nail is cannulated, the cannulation is at least partially threaded to receive a coaxial set screw,
   the intramedullary nail includes at least one oblique slotted bore in communication with the cannulation, the at least one oblique slotted bore receiving the sliding sleeve, and
   the intramedullary nail includes a threaded notch compatible with the lateral set screw.

3. An intramedullary osteosynthetic device according to claim 2, wherein the sliding sleeve comprises a tube having the internal flat and has external threads at a rear of the sliding sleeve engaging the lateral set screw.

4. An intramedullary osteosynthetic device according to claim 2, wherein the coaxial set screw fixes the sliding sleeve to the intramedullary nail by tightening the sliding sleeve inside the oblique slotted bore.

5. An intramedullary osteosynthetic device according to claim 1, wherein:
   the step helix consists of at least two helical twisted step blades attached to a slotted base, and
   wherein the slotted base has a frontal peg fitting into a notch located on the shaft of the hip helical implant.

6. An insertion tool for inserting a hip helical implant having a shaft, comprising:
   a cannulated shaft having a rotating handle;
   an axial insert; and
   a rear cap,
   wherein the cannulated shaft at a front end has a slot engaging a slot on a base of a step helix,
   wherein the rotating handle is assembled over the cannulated shaft, and a rear portion of the cannulated shaft has a nose that can be hammered to remove the insertion tool after the hip helical implant has been inserted;

wherein the step helix has at least two helical twisted step blades attached to a slotted base, and wherein the slotted base has a frontal peg fitting into a notch located on the shaft of the hip helical implant.

7. An insertion tool for inserting the a hip helical implant according to claim 6, wherein the axial insert having a lesser diameter than the cannulated shaft so as to slidably pass through the cannulation of the shaft and having an externally threaded front end engages an internal thread of a shaft of the hip helical implant firmly attaching the insertion tool to the hip helical implant.

8. An insertion tool for inserting the a hip helical implant according to claim 6, wherein the insertion tool, step helix and hip helical implant are assembled prior to insertion.

9. An assembly according to claim 8, wherein assembly of the insertion tool, step helix and hip helical implant comprises:

firmly attaching the step helix to a rear portion of the hip helical implant, such that pegs on the step helix are inserted into holes located on blades of the hip helical implant;

the cannulated shaft of the insertion tool engages the base of the step helix by a slotted mechanism;

the axial insert passes through a cannulation of the base of the step helix and into an internally threaded hole of the shaft of the hip helical implant, wherein the axial insert is threaded into the hip helical implant; and the rear cap of the insertion tool is attached to a threaded rear end of the axial insert.

10. A method of inserting a hip helical implant into a femoral head, comprises the steps of:

introducing an intramedullary nail into a femoral medullary canal;

attaching a hip helical implant via a step helix and axial insert to an insertion tool, the hip helical implant having an external flat corresponding to an internal flat in a sliding sleeve, a lateral set screw affixing the sliding sleeve to the intramedullary nail being parallel but not coaxial to the sliding sleeve;

inserting the hip helical implant through an oblique bore of the intramedullary nail, wherein blades of the hip helical implant pass through slots in the intramedullary nail, wherein blades of the step helix pass through the slots of the intramedullary nail in a same direction as the hip helical implant until hip helical implant reaches a final position inside the femoral head; and after insertion of the hip helical implant the step helix and insertion tool are removed.

11. A method of inserting a hip helical implant into a femoral head according to claim 10, wherein removal of the step helix and insertion tool includes the steps of:

removing a rear cap of the insertion tool;

hammering a nose on a shaft of the insertion tool causing the step helix and insertion tool to disengage from the axial insert and hip helical implant; and unscrewing the axial insert from the hip helical implant, leaving only the hip helical implant in the femoral head with a shaft of the hip helical implant passing through the oblique bore of the intramedullary nail.

12. A method of inserting a hip helical implant into a femoral head according to claim 10, wherein the hip helical implant comprises:

a frontal helical portion having a truncated conical shape;

at least two helical twisted blades attached to the frontal helical portion; and a rear smooth shaft, the shaft having the external flat surface, wherein each blade has a hole for receiving a peg from a step helix fixating the hip helical implant to the step helix, and the hip helical implant is cannulated to receive a Kirschner wire.

13. A method of inserting a hip helical implant into a femoral head according to claim 10, wherein:

the intramedullary nail is cannulated, the cannulation is at least partially threaded to receive a coaxial set screw, the oblique slotted bore is in communication with the cannulation, the oblique slotted bore receiving the sliding sleeve, and the intramedullary nail includes a threaded notch compatible with the lateral set screw.

14. A method of inserting a hip helical implant into a femoral head according to claim 10, wherein the sliding sleeve comprises a tube having the internal flat corresponding to the external flat of the hip helical implant and has external threads at the rear of the sleeve engaging the lateral set screw.

\* \* \* \* \*

UNITED STATES PATENT AND TRADEMARK OFFICE
CERTIFICATE OF CORRECTION

PATENT NO.         : 8,353,910 B2  
APPLICATION NO.    : 12/294567  
DATED              : January 15, 2013  
INVENTOR(S)        : Dell'Oca It is certified that error appears in the above-identified patent and that said Letters Patent is hereby corrected as shown below:

Claim 1, Col. 8, Line 32 should be replaced as follows:

-- step helix for fixating the hip helical implant to the step --

Signed and Sealed this  
Twelfth Day of March, 2013

Teresa Stanek Rea  
*Acting Director of the United States Patent and Trademark Office*